United States Patent [19]
Weinberg et al.

[11] Patent Number: 5,144,946
[45] Date of Patent: Sep. 8, 1992

[54] COMBINED PACEMAKER SUBSTRATE AND ELECTRICAL INTERCONNECT AND METHOD OF ASSEMBLY

[75] Inventors: Alvin H. Weinberg, Moorpark; Robert E. Maston, Aptos, both of Calif.

[73] Assignee: Siemens Pacesetter, Inc., Sylmar, Calif.

[21] Appl. No.: 740,533

[22] Filed: Aug. 5, 1991

[51] Int. Cl.$^5$ ............................................. A61N 1/375
[52] U.S. Cl. ................................................. 178/419 P
[58] Field of Search ........ 128/419 P, 419 PG, 419 PS

[56] References Cited

U.S. PATENT DOCUMENTS

| | | | |
|---|---|---|---|
| 3,822,707 | 7/1974 | Adducci et al. | 128/419 P |
| 3,884,243 | 5/1975 | Cywinski | 128/419 PS |
| 4,026,726 | 5/1977 | Carney | 136/202 |
| 4,041,956 | 8/1977 | Purdy et al. | 128/419 P |
| 4,127,134 | 11/1978 | Ushakoff | 128/419 P |
| 4,254,775 | 3/1981 | Langer | 128/419 PS |
| 4,262,673 | 4/1981 | Kinney | 128/419 P |
| 4,399,819 | 4/1983 | Cowdgry | 128/419 P |
| 4,441,498 | 4/1984 | Nordling | 128/419 P |
| 4,614,194 | 9/1986 | Jones et al. | 128/419 P |
| 4,616,655 | 10/1986 | Weinberg et al. | 128/419 P |

FOREIGN PATENT DOCUMENTS

| | | |
|---|---|---|
| 3507092 | 8/1986 | Fed. Rep. of Germany . |
| 256652 | 5/1988 | Fed. Rep. of Germany . |
| 2380649 | 8/1978 | France . |

OTHER PUBLICATIONS

Bak, David J., "3-D Circuit Boards Optimize Use of Space", *Design News* (Sep. 19, 1988), pp. 146-147.
MacCorquodale, Sharon, "Update: Three-Dimensional Molded Interconnect", *Connection Technology* (Jun. 1990), pp. 23-25.
Allen-Bradley, "Single-and Multilayer Molded Circuits Using Image Decals in the Molding Process", *Electronic Manufacturing* (Jul. 1990), pp. 24-27.
Rose, Jennifer, "Molded Circuit Boards—Structure and Function Become One", *Connection Technology* (Jan. 1989), pp. 21-24.
Simmons, A. E., "New Approaches to Electronic Packaging Utilizing Molded Circuit Technology", *Electronic Manufacturing* (Jun. 1990), pp. 19-22.
Keeler, Robert, "Users Solve 3-D Packaging Problems", *Electronic Packaging & Production* (May 1990), pp. 56-60.
Allen-Bradley, "Molded Packaging Process Combines Circuit Board and Housing", *Electronic Manufacturing* (Nov. 1988) p. 18.

Primary Examiner—William E. Kamm
Attorney, Agent, or Firm—Lisa P. Weinberg

[57] ABSTRACT

A pacemaker having a single integrated interconnect structure is disclosed which combines the functions of a flexible interconnect cable and a protective lid for a hybrid substrate. The integrated interconnect structure is a molded three-dimensional part having a lid portion and a feedthrough portion. An electronic substrate can be mounted onto the integrated interconnect structure wherein electrical conductors formed within the integrated interconnect structure connect the electronic substrate to the battery terminals and to the pacemaker feedthroughs. In one embodiment, the integrated interconnect structure may be adapted to have additional electronic circuitry mounted directly onto a flat inner cavity within the lid portion, thereby enabling electronic components to be easily added or modified without complicating the assembly operations of the pacemaker.

27 Claims, 3 Drawing Sheets

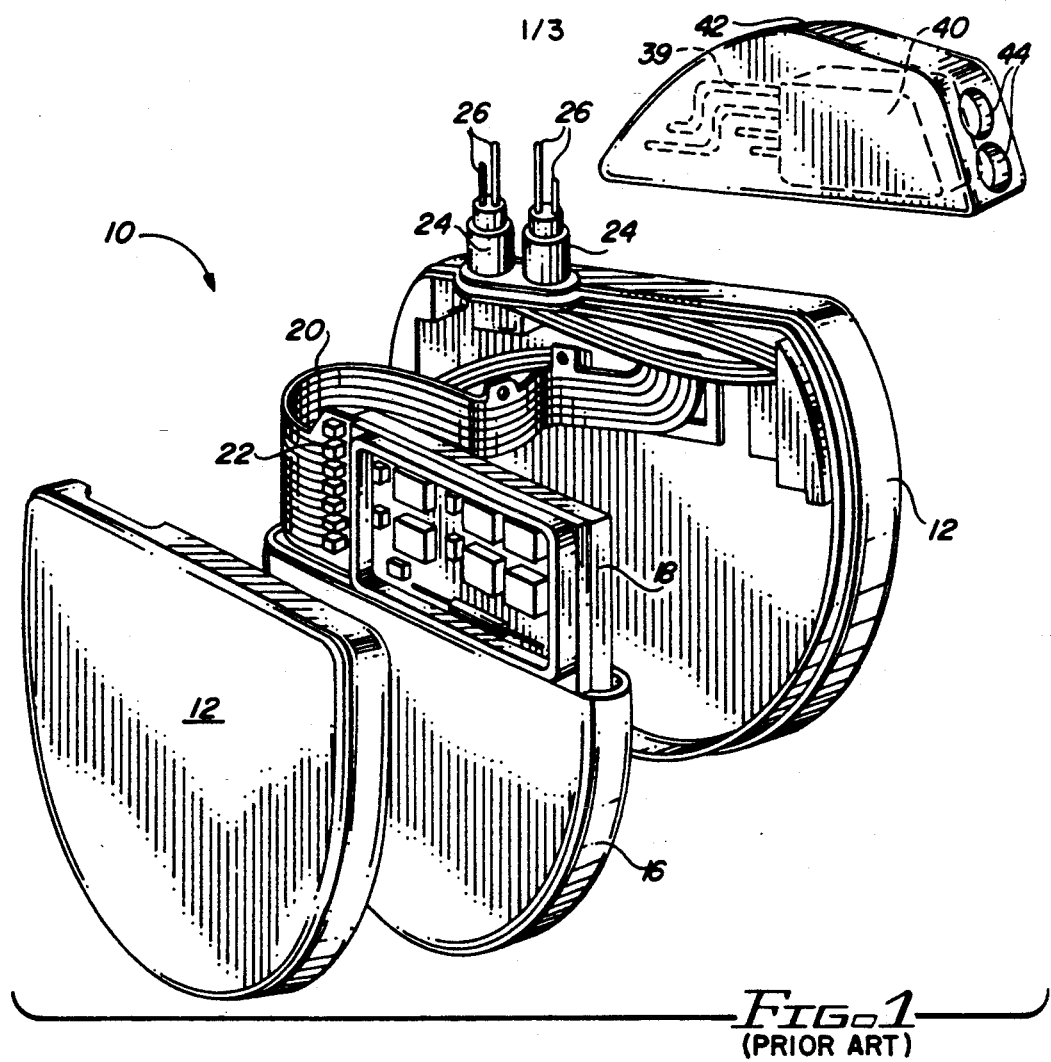
FIG. 1 (PRIOR ART)
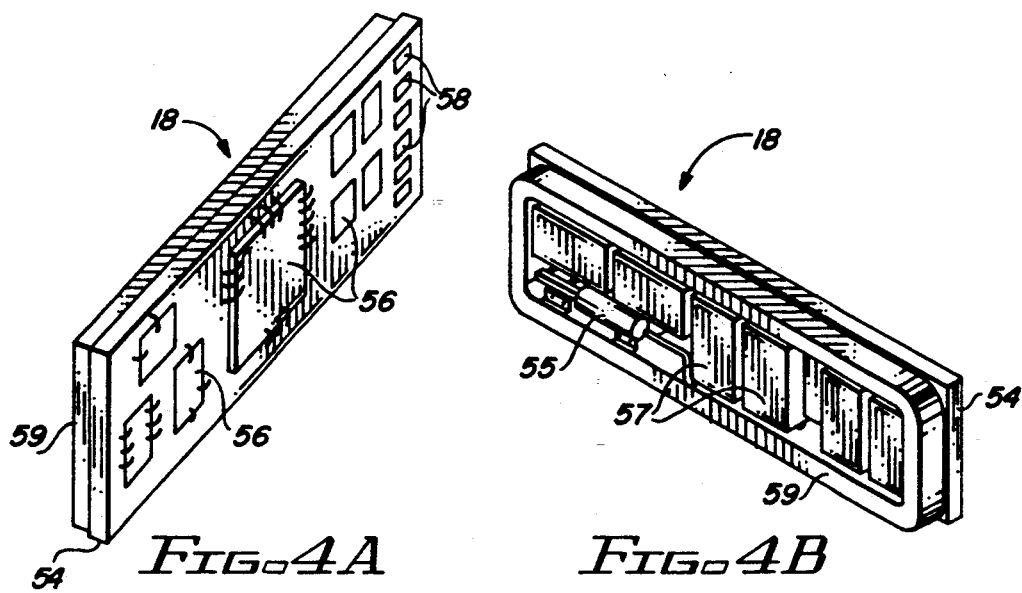
FIG. 4A    FIG. 4B

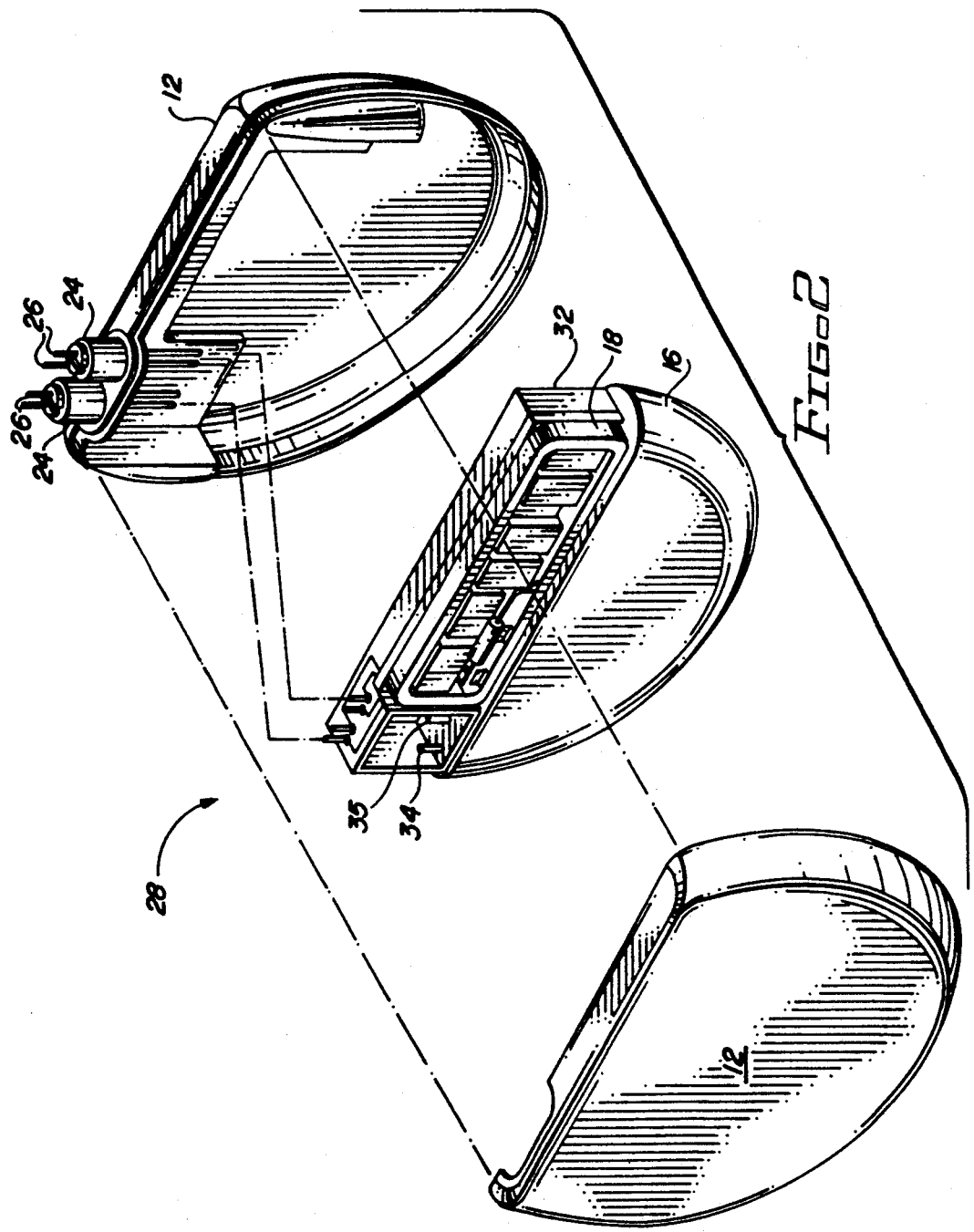

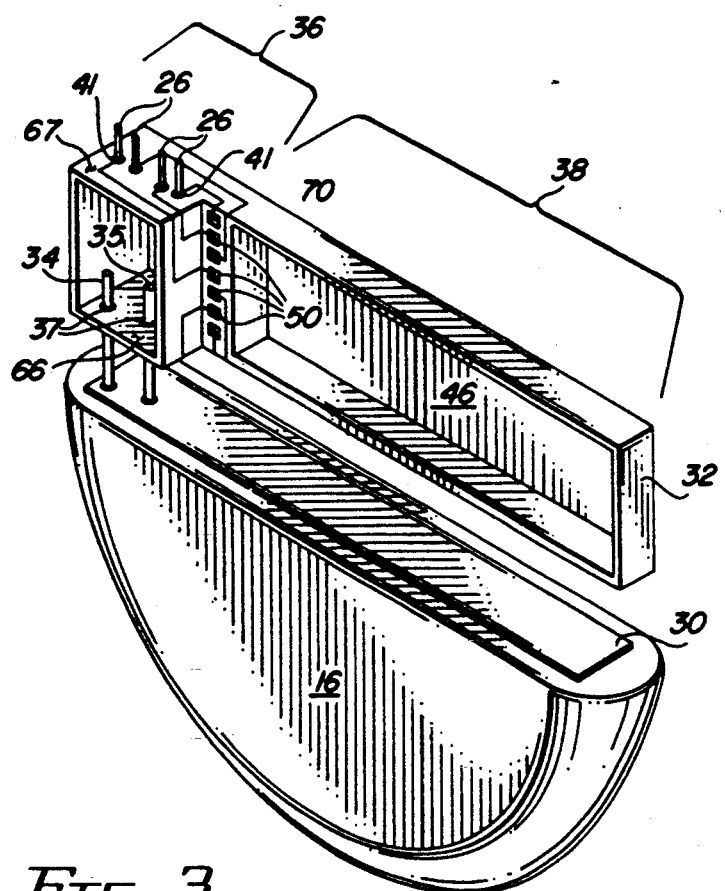
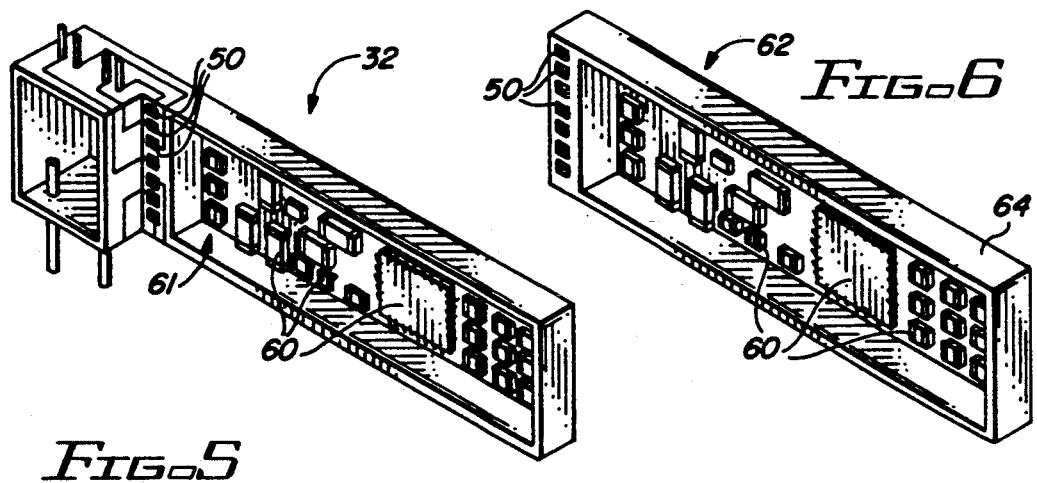

COMBINED PACEMAKER SUBSTRATE AND ELECTRICAL INTERCONNECT AND METHOD OF ASSEMBLY

FIELD OF THE INVENTION

The present invention relates to pacemakers, and, more particularly, to a microelectronic package for mounting electronic components for use in a pacemaker and a method of manufacturing a pacemaker.

BACKGROUND OF THE INVENTION

There are three primary driving forces for today's implantable biomedical devices increased functionality, enhanced reliability, and a reduction in product size. The advent of the hybrid microcircuit has been one of the major contributors to meeting all of these requirements, thus enabling the development of sophisticated implantable products which are truly physiologically compatible in terms of product size.

A problem exists in the pacemaker field in that currently available pacemaker designs utilize discrete substrates and lids to protect and enclose microcircuit components. Furthermore, the pacemaker assembly employs flexible interconnect circuitry to connect the microcircuit components in the electronic package to the pacemaker battery and output feedthroughs. The assembly of such a pacemaker consequently requires accurate placement of several discrete structures which is costly to assemble and difficult to automate.

Another problem of the prior art pacemaker is that design changes during the qualification and testing phases of pacemaker development often necessitate adding additional components. In many cases, these components circuitry due to the lack of flexible interconnect circuitry due to the lack of real estate on the hybrid substrate, which significantly complicates the assembly of the pacemaker and potentially decreases the reliability of the system.

It is therefore an objective of the present invention to provide a new and improved electronics package that combines the functions of the hybrid lid and the flexible interconnect circuit into a single structure.

It is also an objective of the present invention to provide an interconnect structure which can easily add electronic components without complicating the assembly operations of the pacemaker.

It is another objective to provide a pacemaker which has significantly improved reliability, and is easily manufactured at a reduction of cost.

SUMMARY OF THE INVENTION

The disadvantages and limitations of the background art discussed above are overcome by the present invention. According to the invention, an arrangement is provided which enables the rapid and effective assembly of an implantable medical device such as a pacemaker. The solution offered by the present invention is to combine the functions of a protective cover for a hybrid substrate and the flexible interconnect circuitry into an integrated interconnect structure.

In accordance with one embodiment of the present invention, a pacemaker is provided comprising an electronic module, a battery having battery terminals for interconnecting the battery with the electronic module, and a pacemaker housing for housing the battery and the electronic module. The housing includes electrical feedthroughs which serve to interconnect the electronic module with a pacemaker lead. The electronic module includes a circuit substrate and an integrated interconnect structure. The circuit substrate has electronic components mounted thereon. The integrated interconnect structure is a three-dimensional molded part which combines the function of a lid for the circuit substrate and the function of the flexible interconnect circuitry between the battery, the circuit substrate, and the electrical feedthroughs. Interconnect conductors may be formed within and/or otherwise printed on any of the surfaces of the integrated interconnect structure. The integrated interconnect structure further includes means for receiving the battery feedthroughs and the electrical feedthroughs.

In accordance with another embodiment of the present invention, an electronic module for use in a pacemaker is provided. The electronic module comprises a substrate, an integrated interconnect structure, and electronic components. The integrated interconnect structure is comprised of an electrically insulating material which is moldable into a three-dimensional part. The electronic components are mounted either onto the substrate, onto the integrated interconnect structure, or both. In one embodiment, all of the active components (i.e., diodes, transistors, and other integrated circuits) are placed on one side of the substrate. The integrated interconnect structure, which includes a cavity for receiving the substrate, thus serves as a lid or cover for the active electrical components which are mounted onto the substrate. The integrated interconnect structure further includes conductors and through-holes integrally formed therein, which serve to interconnect the electronic module to battery feedthroughs and electrical feedthroughs in the pacemaker.

In accordance with another embodiment of the present invention, an integrated interconnect structure for use with a pacemaker is provided. The integrated interconnect structure comprises a three-dimensional molded part having a lid portion and a feedthrough portion. The lid portion includes a flat inner cavity with walls extending therefrom for receiving and protecting an electronic substrate. The feedthrough portion includes several through-holes adapted to receive battery terminals and electrical feedthroughs. Conductors are integrally formed within the integrated interconnect structure such that the electronic substrate may be electrically interconnected to the battery terminals and to the electrical feedthroughs. Advantageously, the integrated interconnect structure combines the functions of the hybrid lid and the flexible interconnect circuit into a single structure. The lid portion may further be adapted to have additional electronic circuitry mounted directly onto the flat inner cavity thereby enabling electronic components to be easily added or modified without complicating the assembly operations of the pacemaker.

In accordance with one method of the present invention, a method of manufacturing a pacemaker is disclosed which comprises the steps of, first, providing a battery with battery terminals and electrical feedthroughs which extend through a pacemaker housing. Electronic components are then mounted onto a substrate. The substrate is then mounted onto an integrated interconnect structure to form an electronic module. The electronic module is next mounted on the top of the battery so that the battery terminals extend through two of the through-holes. Finally, the battery, the integrated interconnect structure, and the electronic module are positioned within the pacemaker housing with the feedthroughs extending through additional through-holes within the integrated interconnect structure. Advantageously, by reducing the number of components (i.e., by eliminating a separate flex circuit), the integrated interconnect structure provides greatly improved and accelerated assembly of device components, increased reliability of these connections, and reduced cost of manufacturing due to its simplicity, and the ability to automate the assembly process.

Finally, all of the aforesaid advantages and objectives are achieved without incurring any substantial relative disadvantage. It will, therefore, be perceived that the advantages of the present invention result in rapid and effective assembly of a cardiac pacemaker, making the method of the present invention a highly desirable enhancement to implantable cardiac pacemaker therapy.

BRIEF DESCRIPTION OF THE DRAWINGS

Further features and advantages of the present invention may be more readily understood by reference to the following description taken in conjunction with the accompanying drawings, in which:

FIG. 1 is an exploded perspective view of a pacemaker known in the prior art;

FIG. 2 is an exploded perspective view of a pacemaker incorporating the present invention;

FIG. 3 is a partial perspective view of one embodiment of the present invention;

FIGS. 4A and 4B are two side views of a circuit package for use with the present invention shown in FIG. 3;

FIG. 5 is a perspective view of another embodiment of the present invention; and FIG. 6 is a perspective view of another embodiment of the present invention.

DETAILED DESCRIPTION OF THE INVENTION

Although the present invention will be described with reference to the embodiments shown in the drawings, it should be understood that various modifications can be incorporated into the present invention. The foregoing general description and the following detailed description are exemplary and explanatory but are not to be restrictive of the invention. The accompanying drawings illustrate one of the embodiments of the invention, and, together with the description, serve to explain the principles of the invention in general terms. In addition, any suitable size, shape, or type of elements or materials can be used. Like numerals refer to like parts throughout the disclosure.

In FIG. 1, there is shown an exploded perspective view of a pacemaker 10 known in the prior art. The pacemaker 10 generally comprises a housing 12, a battery 16, electronic package 18, and ribbon or flex cable 20 connected between the electronic package 18, at electrical connections 22, and feedthroughs 24 at electrical feedthrough leads 26. An interior end of each of the electrical feedthrough leads 26 is suitably connected, such as by soldering, to an end of the flex cable 20. An opposite end of the electrical feedthrough leads 26 is positioned for engagement with an associated conductor 39 of a connector block 40 within a connector top 42 intended for suitable mounting on the top surface of the housing 12. Proximal ends of the pacemaker leads (not shown) are received through suitable jack openings 44 in the connector top 42 for electrical connection with the connector block 40. The distal ends of the pacemaker leads (not shown) are suitably attached to the heart of a patient. The battery 16 has two terminals (not shown) that extend up from its top which are connected to the electronic components of the electronic package 18 either by way of the flex cable 20 or individual discrete wires. The electronic package 18 is fixedly connected to the top of the battery 16. One of the major problems of the prior art, as exemplified by the device shown in FIG. 1, is that in order to make the electrical connections between the battery 16, the electronic package 18, and the feedthrough leads 26, individual connections had to be made with great precision due to the pacemaker's small size. This, of course, was time-consuming and costly.

In FIG. 2, there is shown an exploded perspective view of one embodiment of the present invention. A pacemaker 28 comprises a housing 12, a battery 16, an electronic package 18, an integrated interconnect structure 32, and feedthroughs 24 at electrical feedthrough leads 26. The battery 16 is of conventional design and has two terminals 34 and 35 extending up from its top surface.

As best seen in FIG. 3, the pacemaker 28 also includes a shock mount pad 30. The shock mount pad 30 rests on top of the battery 16 with the terminals 34 and 35 projecting therethrough. The shock mount pad 30 is generally comprised of silicone rubber, however, any suitable shock absorbing type of material can be provided. In an alternate embodiment of the present invention, the shock mount pad 30 might be replaced by a silicone rubber covering over the integrated interconnect structure 32.

The integrated interconnect structure 32, in the embodiments shown in FIGS. 2 and 3, generally comprises a molded three-dimensional part made of a thermoplastic resin that has been extruded, thermo-formed or injection molded using conventional molding equipment. Several suitable thermoplastic materials are currently available, including polyetherimide sold under the trademark ULTEM and manufactured by General Electric; polyethersulfone sold under the trademark VICTREX manufactured ICI Americas, Inc.; or any equivalent plastic material having the following properties: high-strength, low dielectric constant, low coefficient of thermal expansion, and can meet the molding and soldering requirements.

Conductors may be injection molded into the integrated interconnect structure 32 or printed on any of the flat surfaces of the integrated interconnect structure 32 using one of several methods, such as metal stamping, printing conductive inks, or using additive plating. For a further explanation of three-dimensional molded processes, reference is made to the following publications: "3-D Circuit Boards Optimize Use of Space," *Design News*, Sep. 19, 1988, pp. 146–147; and "Update: Three-Dimensional Molded Interconnect," *Connection Technology*, June 1990, pp. 23–25; and "Single- and Multilayer Molded Circuits Using Image Decals in the Molding Process," *Electronic Manufacturing*, July 1990, pp. 24–27; which publications are hereby incorporated herein by reference.

The purposes of the integrated interconnect structure 32 includes providing protection for the electronic package 18 and providing electrical interconnections between the electronic package 18, the battery 16, and the electrical feedthrough leads 26. Thus, in the preferred embodiment shown in FIG. 3, the integrated interconnect structure 32 has a feedthrough portion 36 and a lid portion 38. The feedthrough portion 36 has a hollow interior with two feedthrough holes 37 extending through a bottom wall 66 and four feedthrough holes 41 extending through a top wall 67. In a preferred embodiment of the invention, the battery terminals 34 and 35 and the electrical feedthrough leads 26 are located in each of the feedthrough holes 37 and 41 to make good electrical contact with the integrated interconnect structure 32.

The lid portion 38 has a general box-like shape with an interior recess 46. In the embodiment shown, a plurality of contacts 50 are disposed for making electrical contact with corresponding contacts (not shown) on the electronic package 18. The contacts 50 may be comprised of any suitable type of contact material.

In the embodiment shown, the integrated interconnect structure 32 has a plurality of conductors or conductive strips 70 integrally formed therewith. The conductors 70 are generally provided to function as electrical connections between the contacts 50 and the battery terminals 34 and 35, and the electrical feedthrough leads 26. In one embodiment of the invention, the conductors 70 are comprised of electrical wires which the dielectric material of the integrated interconnect structure 32 is molded around. In another embodiment of the present invention, the integrated interconnect structure 32 is comprised of a molded circuit assembly board which has conductive traces printed thereon. The conductive traces follow the contours of the outer surface of the integrated interconnect structure 32 to interconnect the contacts 50 with the electrical feedthrough leads 26 and the battery terminals 34 and 35.

In FIGS. 4A and 4B, two sides are shown of an electronic package 18 intended to be used with the integrated interconnect structure 32 shown in FIG. 3. In the preferred embodiment shown in FIGS. 4A and 4B, the substrate 54 is a double-sided substrate. On one side (FIG. 4A), the electronic package 18 includes electronic components 56 (including, diodes, transistors, and other integrated circuits) mounted onto a substrate 54 and contacts 58. As shown in FIG. 4B, components which do not need to be protected (such as a crystal 55, tantalum capacitors 57, and a telemetry coil 59), are placed together on the other side of the substrate 54. The electronic components 55, 56, 57 and 59 are fixedly connected to the substrate 54 with interconnect metallization (not shown) within the substrate 54 thereby interconnecting the electronic components together. The interconnect metallization also interconnects the electronic components 55, 56, 57 and 59 with the contacts 58. The contacts 58 are located at a side region of the substrate 54 and are intended to make electrical contact with the contacts 50 of the integrated interconnect structure 32 shown in FIG. 3. Thus, when the substrate 54 is mounted onto the integrated interconnect structure 32, all of the active components will be protected by the integrated interconnect structure 32.

The electronic package 18 can be connected with the integrated interconnect structure 32 by merely inserting the side of the electronic package 18 having the active electronic components into the interior recess 46 of the integrated interconnect structure 32. The substrate 54 is suitably sized and shaped to align the contacts 58 with the contacts 50 as the electronic package 18 is mounted to the integrated interconnect structure 32. The electronic package 18 can then be fixedly connected to the integrated interconnect structure 32 by any suitable means. For example, the integrated interconnect structure 32 may be attached to the substrate using a nonconductive sealant, while the contacts 50 and 58 may be connected by welding, solder or epoxy.

Once the electronic package 18 is mounted, the integrated interconnect structure 32 is easily aligned over the battery 16 such that the battery terminals 34 and 35 can be inserted through the through-holes 37 and subsequently soldered or otherwise welded. One end of the electrical feedthrough leads 26 is also easily positioned for engagement with the feedthrough holes 41. Thus, the integrated interconnect structure 32 interconnects the electronic package 18 to the battery terminals 34 and 35 and to the electrical feedthrough leads 26.

Advantageously, the integrated interconnect structure 32 is also capable of mounting additional electronic components on the interior recess 46, as shown in FIG. 5. In the embodiment shown, an integrated interconnect structure 32 is provided with electronic components 60 connected directly onto the interior recess 46 (shown in FIG. 3). The integrated interconnect structure 32 has suitable conductive traces on its interior recess 46 to interconnect the electronic components 60. Thus, no additional circuit package need be connected to the integrated interconnect structure 32. However, the embodiment shown in FIG. 5 allows for an additional electronic substrate, such as the electronic package 18 shown in FIG. 4, to be connected to the integrated interconnect structure 32. For this purpose, the integrated interconnect structure 32 has contacts 50 and suitable space is provided in the area 61 to position additional electronic components therein. This provides the additional capacity for providing not only passive components, such as capacitors and resistors to the integrated interconnect structure 32, but it also enables active components, such as diodes, FETS, and other integrated circuits to be mounted to the integrated interconnect structure 32. Thus, this allows the electronics of a pacemaker having the integrated interconnect structure 32 to be modified at a later date without having to change the basic integrated interconnect structure 32.

In FIG. 6, there is shown an another alternate embodiment of the present invention. In the embodiment shown, an integrated interconnect structure 62 is provided without a feedthrough connection section. Thus, the integrated interconnect structure 62 merely comprises an electronic connection section 64. The integrated interconnect structure 62 has electronic components 60 connected thereto and suitable conductive traces (not shown) interconnecting the electronic components 60 and connecting the electronic components 60 to contacts 50. For the embodiment shown, the integrated interconnect structure 62 would be connected to the battery terminals 34 and 35 and the feedthrough leads 26 as known in the prior art by means of a flex cable as shown in FIG. 1. Advantageously, the integrated interconnect structure 62 in the embodiment shown, unlike the prior art shown in FIG. 1, is adapted to receive an additional electronic substrate such as substrate 52 shown in FIG. 4. Thus, the integrated interconnect structure 62 can have an additional electronic substrate connected thereto to provide increased or additional features to a pacemaker, similar to the integrated interconnect structure 32 shown in FIG. 5.

There are two major advantages provided by the present invention. First, the use of the integrated interconnect structure allows for the elimination of the use of wires and flex cables in making electrical connections. The integrated interconnect structure of the present invention, due to its modular feature of electrical interconnection, allows for connections to be made relatively simply and easily by merely positioning the battery terminals and feedthrough leads in the appropriate integrated interconnect structure holes. This is also obviously faster than the flex cable connections in prior art devices. This also allows for the assembly process to become automated due to its simplicity of assembly.

Second, the three-dimensional integrated interconnect structure is a modular unit that can have additional circuit packages connected thereto. This has never been provided in pacemakers and can be used to add additional features and functions to pacemakers without having to redesign the entire pacemaker. The added space for locating electronic components can also allow for Z-axis integration of electronic components that has not been available in the prior art.

Let it be understood that the foregoing description is only illustrative of the invention. Various alternatives and modifications can be devised by those skilled in the art without departing from the spirit of the invention. Accordingly, the present invention is intended to embrace all such alternatives, modifications and variances which fall within the scope of the appended claims.

What is claimed is:

1. A pacemaker comprising:
    a housing;
    at least one electrical feedthrough terminal extending through the housing;
    a battery located in the housing, the battery having two terminals extending out of a top of the battery;
    an electronic substrate having electronic components mounted thereon; and
    a molded integrated interconnect structure having a lid portion, at least a first, a second and a third through-hole, and conductive means integrally formed therein, the lid portion having means for receiving and protecting the electronic substrate, the first and second through-holes being connected to one each of the battery terminals, the third through-hole being connected to the electrical feedthrough terminal, the conductive means including means for electrically interconnecting the electronic substrate to the battery terminals and to the electrical feedthrough terminal.

2. The pacemaker, as recited in claim 1, further comprising:
    electronic components mounted onto the integrated interconnect structure.

3. The pacemaker, as recited in claim 2, wherein the conductive means comprises:
    means for electrically connecting the electronic components of the electronic substrate to the electronic components mounted onto the integrated interconnect structure.

4. The pacemaker, as recited in claim 3, wherein the means for receiving and protecting the electronic substrate comprises a circuitry housing recess.

5. The pacemaker, as recited in claim 4, wherein the electronic components mounted onto the integrated interconnect structure are mounted within the circuitry housing recess.

6. The pacemaker, as recited in claim 1, wherein:
    the integrated interconnect structure has a first set of electrical contacts on a surface thereof; and
    the electronic substrate has a second set of electrical contacts on a surface thereof for making electrical contact with the first set of electrical contacts.

7. The pacemaker, as recited in claim 1, further comprising:
    a shock mount pad between the substrate and battery.

8. The pacemaker, as recited in claim 1, wherein the integrated interconnect structure is comprised of a molded dielectric material.

9. The pacemaker, as recited in claim 8, wherein the conductive means comprises:
    conductive wires molded within the dielectric material.

10. The pacemaker, as recited in claim 8, wherein the conductive means comprises:
    conductors printed on the surfaces of the molded dielectric material.

11. An electronic module for use with a pacemaker, the pacemaker having a battery with terminals, and at least one electrical feedthrough terminal for connection to a pacing lead, the electronic module comprising:
    an electronic substrate having electronic components mounted thereon; and
    an integrated interconnect structure having a recess for receiving and protecting the electronic substrate, the integrated interconnect structure further having conductive means for electrically connecting the electronic substrate to the battery and feedthrough terminals.

12. The electronic module, as recited in claim 11, further comprising:
    electronic components mounted onto the recess of the integrated interconnect structure; and
    wherein the conductive means includes means for electrically interconnecting the electronic components mounted onto the integrated interconnect structure with the electronic components mounted on the electronic substrate.

13. The electronic module, as recited in claim 11, wherein the conductive means comprises:
    conductive through-holes for passage of the battery terminals and at least one feedthrough terminal therethrough.

14. The electronic module, as recited in claim 11, wherein the conductive means comprises:
    conductors substantially contained inside the integrated interconnect structure with the dielectric polymer material molded thereover.

15. The electronic module, as recited in claim 11, wherein the conductive means comprises:
    conductors printed on the surfaces of the molded dielectric material.

16. The electronic module, as recited in claim 11, wherein the conductive means comprises:
    electrical contact means for connecting the electronic substrate to the integrated interconnect structure.

17. The electronic module, as recited in claim 11, wherein the an integrated interconnect structure is comprised of a molded dielectric polymer material.

18. An electronic package for use within a pacemaker, the pacemaker having a battery and feedthroughs, the package comprising:
    an integrated interconnect structure having a recess for at least partially housing an electronic substrate, the integrated interconnect structure having conductive means integrally formed therewith;

electronic components mounted onto the recess of
  integrated interconnect structure and electrically
  interconnected by the conductors; and
means for connecting an electronic substrate to the
  integrated interconnect structure and the conductive means.

19. The package, as recited in claim 18, wherein the conductive means comprises:
  conductive holes for receiving and making electrical connection with the battery terminals.

20. The package, as recited in claim 18, wherein the conductive means comprises:
  conductive holes for receiving and making electrical connection with the feedthroughs.

21. An electronic package for use with a pacemaker, the pacemaker including a battery having battery terminals, an electronic substrate, and feedthrough terminals for connection with a pacemaker lead, the package comprising:
  a integrated interconnect structure having a recess for receiving and protecting the electronic substrate, the integrated interconnect structure further having conductive means for electrically connecting the electronic substrate to the battery and feedthrough terminals.

22. The package, as recited in claim 21, further comprising electronic components mounted onto the recess of the integrated interconnect structure and electrically interconnected by the conductive means.

23. The package, as recited in claim 21, wherein the integrated interconnect structure has conductive holes for receiving and making electrical connection with the battery terminals.

24. The package, as recited in claim 21, wherein the integrated interconnect structure has conductive holes for receiving and making electrical connection with the feedthroughs.

25. The package, as recited in claim 21, wherein the integrated interconnect structure is comprised of a molded dielectric polymer material.

26. A method of manufacturing a pacemaker comprising steps of:
  providing a battery with battery terminals;
  providing electrical feedthroughs extending through a pacemaker housing;
  mounting electronic components onto a substrate;
  mounting the substrate onto an integrated interconnect structure to form an electronic module, the interconnect structure comprising dielectric material having a cavity molded therein and conductors integrally formed therewith, the interconnect structure further having a plurality of through-holes molded therein for the positioning of the battery terminals and the electrical feedthroughs;
  mounting the electronic module on the top of the battery so that the battery terminals extend through two of the plurality of through-holes; and
  positioning the battery, the integrated interconnect structure and the electronic module in the pacemaker housing with the feedthroughs extending through the housing into through-holes within the integrated interconnect structure.

27. The method, as recited in claim 26, comprising steps of:
  mounting electronic components onto the cavity molded within the integrated interconnect structure.

* * * * *